United States Patent [19]

Barnett et al.

[11] 4,129,645

[45] Dec. 12, 1978

[54] SUNSCREEN COMPOSITIONS

[75] Inventors: Gabriel Barnett, New York; Nathan Gershaw, Commack; Jack J. Mausner, East Hills, all of N.Y.

[73] Assignee: Helena Rubinstein, Inc., New York, N.Y.

[21] Appl. No.: 788,885

[22] Filed: Apr. 19, 1977

Related U.S. Application Data

[63] Continuation-in-part of Ser. No. 611,435, Sep. 5, 1975, Pat. No. 4,087,555.

[51] Int. Cl.² ............................................. A61K 7/44
[52] U.S. Cl. ...................................... 424/60; 424/59; 424/357; 424/359
[58] Field of Search ................................. 424/60, 59

[56] References Cited

U.S. PATENT DOCUMENTS

| | | | |
|---|---|---|---|
| 3,689,678 | 9/1972 | Fox et al. | 424/365 |
| 3,780,195 | 12/1973 | Balassa | 424/365 |
| 3,947,571 | 3/1976 | Murphy et al. | 424/64 |
| 3,957,969 | 5/1976 | Fujujama et al. | 424/365 |
| 3,959,491 | 5/1976 | Young et al. | 424/365 |

*Primary Examiner*—Dale R. Ore
*Attorney, Agent, or Firm*—Burgess, Ryan and Wayne

[57] ABSTRACT

Sunscreen compositions in the form of a skin softening moisturizing base with at least a part of the sunscreening active ingredient encapsulated in a hectorite clay capsule.

7 Claims, No Drawings

SUNSCREEN COMPOSITIONS

CROSS-REFERENCE TO RELATED APPLICATION

This application is a continuation-in-part of co-pending application Ser. No. 611,435, filed Sept. 5, 1975, now U.S. Pat. No. 4,087,555.

BACKGROUND OF THE INVENTION

The present invention relates to a sunscreen composition and, more particularly, the present invention relates to a cosmetic preparation for application to the skin for protecting the user against the harmful effects of exposure to the sun.

Nowadays, many people wish to appear tanned because they have equated a deep rich tanned look with health and well-being. In an attempt to acquire the tanned look, many procedures have been suggested. These include, for example, various cosmetic preparations for dyeing or staining the skin. Such preparations, however, may color the skin temporarily, but the coloring agent either washes off or wears off. While many of these preparations provide a natural-looking tan, others provide a coloration which is uneven and unnatural-looking. Many people prefer direct exposure to the sun for acquiring a "healthy" tan.

Direct exposure to the sun can be tolerated by some people whose natural pigmentation protects them against the harmful effects of the solar radiation. Other people, however, are easily burned and cannot tolerate prolonged exposure to the sun. The recommended procedure for acquiring a tan, therefore, is to expose ones skin to the sun for only a short duration each day for a period of several days or weeks until the tan is acquired. This procedure is not convenient for those people who may expose themselves to the sun only on weekends or infrequently. Thus, compositions have been formulated for application to the skin to filter out a large amount of the ultraviolet radiation so that exposure for several hours will still provide the effect of exposure for a short period of time. These compositions are well known in the art and are all based on one or more known sunscreening agents. Some of these compositions are formulated as liquids for application to the skin and others are formulated as creams. They all suffer from one or more disadvantages in lack of ease of application, having a base which is easily washed off the skin upon contact with water, or unusual difficulty in removing them from the skin when their effect is no longer needed.

SUMMARY OF THE INVENTION

It is, therefore, the primary object of the present invention to provide a sunscreening composition free of the aforementioned and other such disadvantages.

It is another object of the present invention to provide a sunscreening composition which is easy to apply to the skin and effective in screening the harmful rays of the sun.

It is still a further object of the present invention to provide a sunscreening composition which is effective to filter the harmful rays of the sun while also providing a skin moisturizing base.

It is yet another object of the present invention to provide an effective sunscreening composition in which at least a part of the sunscreening agent is encapsulated.

Consistent with the foregoing objects, the composition of the present invention includes a skin softening moisturizing base and a sunscreening agent. The sunscreening agent can be any one, or a combination, of the well known materials such as 2-ethoxyethyl-p-methoxycinnamate or amyl p-dimethylaminobenzoate. At least a portion of the sunscreening agent is encapsulated in a hectorite clay capsule.

The skin softening moisturizing base is characterized by two distinct phases, with the encapsulated sunscreening agent being considered a third phase. The first, or oil, phase comprises an emollient. Emollients are organic substances having a boiling point higher than water, and these substances remain on the skin as a vehicle for the active ingredients. Suitable emollients for the present invention include, but are not limited to, aliphatic alcohols having 4 to 20 carbon atoms, glycols having 2 to 3 carbon atoms, fatty acids having from 12 to 20 carbon atoms and the esters thereof. These emollients are, for example, isostearyl alcohol, glyceryl monostearate, cetyl alcohol, isopropyl lanolate, isopropyl myristate, isopropyl palmitate, and the like.

While each of these emollients can be employed alone, it is preferable to employ two or more of the emollients in combination. Furthermore, to enhance applicability onto the skin, surfactants are included. Suitable surfactants include, for example, nonionic surfactants or other suitable surfactants known in the emulsion art. See, for example, McCutcheon, "Detergents and Emulsifiers" (1964). In addition, small amounts of preservatives may be included to prevent microbial contamination, and such preservatives illustratively are the alkyl esters of p-hydroxybenzoic acid such as, for example, propyl paraben, methyl paraben, and the like. Furthermore, emulsifying agents may be included to provide a stable emulsion of the oil phase and the water phase, more fully described hereinbelow. It should also be noted that some ingredients may serve a dual purpose of being a surfactant and emulsifying agent or emollient and emulsifying agent. A dispersing agent may also be included.

The second, or water, phase includes a hectorite clay, a peptizer for the clay, a humectant, preservatives, protein for application to the skin, and other suitable ingredients.

Perfumes, coloring agents, and other inert ingredients may be included.

DESCRIPTION OF THE PREFERRED EMBODIMENT

Hectorite clay

The hectorite clays used in this invention are made up of silicon (Si), magnesium (Mg), lithium (Li), oxygen, hydroxyl (OH), may or may not contain fluorine (F), and an exchangeable cation. Exchangeable cations which have been observed are barium, calcium, cesium, hydrogen, lithium, magnesium, potassium, rubidium, sodium and strontium. Sodium and lithium are commonly present as this cation or cations, as two or more may be present.

Van Olphen gives the following general formula for half a unit cell of hectorite clay:

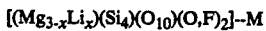

where M is an exchangeable cation. Fluorine (F) may or may not be present. Some hydroxyl is normally present.

Synthetic hectorite clays are available. Because of uniformity in quality and analysis, the synthetic hectorite clays are preferred over the clay derived from natural hectorite clay mineral Some suppliers of synthetic hectorite clay are, LaPorte Industries under the trademark LAPONITE and Baroid Division National Lead Company under the trademark BARASYM. Synthetic hectorite clays can be made by the process disclosed in U.S. Pat. No. 3,586,478, granted to Barbara S. Neumann on June 22, 1971, and which is embodied herein by reference.

The Encyclopedia of Chemical Technology, 2nd Edition, Vol. 5, page 547, gives the following typical formula for hectorite clay, from a natural source:

$$[Mg_{2.67}Li_{0.33}(Na_{0.33})]Si_4O_{10}(OH,F)_2$$

In Table 1, below, there is given the analysis of seven different hectorite clays. No. I is a natural clay and the analysis is taken from Ency. Chem. Tech., 2nd Ed., Vol. 5, page 548. No. II is a beneficiated "90%" content natural hectorite supplied by Baroid under the trademark MACALOID. No's III, IV, and V are synthetic clays supplied by Baroid under the trademark BARASYM. No's VI and VII are synthetic clays supplied by LaPorte under the trademark LAPONITE.

TABLE 1

| Analysis in Wt.% | Hectorite Clays | | | | | | |
|---|---|---|---|---|---|---|---|
| | I | II | III | IV | V | VI | VII |
| $SiO_2$ | 55.9 | 51.9 | 56.2 | 56.1 | 56.1 | 55.9 | 60.4 |
| MgO | 25.0 | 22.1 | 29.2 | 28.4 | 28.4 | 26.7 | 26.0 |
| $Li_2O$ | 1.1 | 1.2 | 2.3 | 2.1 | 0.5 | 1.9 | 1.1 |
| $Na_2O$ | 2.7 | 3.1 | 0.6 | 2.4 | 3.5 | 4.3 | 3.0 |
| F | 6.0 | 2.1 | 1.8 | 1.6 | 1.6 | 8.3 | 0.0 |
| CaO | 0.0 | 6.5 | 0.5 | 0.4 | 0.3 | 0.1 | 0.2 |
| $Fe_2O_3$ | 0.0 | 0.3 | 0.0 | 0.0 | 0.0 | 0.0 | 0.0 |
| $Al_2O_3$ | 0.1 | 0.8 | 0.0 | 0.0 | 0.0 | 0.0 | 0.0 |
| Ignition Loss | 12.1 | 11.7 | 11.4 | 9.5 | 9.5 | 3.6 | 6.9 |

PEPTIZER

It is preferred to work first with a thin (low viscosity) watery fluid composition of clay and water. This is accomplished by having present during the formation of the thin, watery fluid composition an amount of peptizer sufficient to prevent the formation of a gel, or adding sufficient peptizer to an already existing gel to destroy the gel. The thin, watery fluid composition facilitates blending of other components and the filling of the small containers often used in the cosmetics industry; also air bubbles and foaming can be more readily eliminated from the product composition before the filling of, and during the filling of, the containers. The final desired gel condition is produced by heating the fluid aqueous colloidal solution of hectorite clay and peptizer agent (and other components) to a temperature at which the fluid solution changes to a gel.

Any of the known peptizers may be used, such as, ammonia, hydrogen peroxide, sodium carbonate, sodium citrate, sodium hydroxide sodium oxalate, sodium silicate, and water soluble salts of condensed phosphoric acids.

It is preferred to use as the peptizer one or more of the water soluble salts of a condensed phosphoric acid. (This nomenclature is taken from Ency. Chem Tech., 2nd Ed., Vol. 15, pp. 241-257, John Wiley & Sons, 1968). The most preferred salts are water soluble ammonium, potassium, or sodium salts of the condensed phosphoric acid. Illustrative salts are: tetraammonium pyrophosphate; tetrapotassium pyrophosphate; tetrasodium pyrophosphate; ammonium tripolyphosphate; potassium tripolyphosphate; sodium tripolyphosphate; ammonium trimetaphosphate; potassium trimetaphosphate; sodium trimetaphosphate; ammonium tetrametaphosphate; potassium tetrametaphosphate; sodium tetrametaphosphate; and the phosphate glasses, such as, ammonium hexametaphosphate; potassium hexametaphosphate and sodium hexametaphosphate. (Water soluble is intended to mean herein "soluble enough to do the peptizing task".) Tetrasodium pyrophosphate and sodium hexametaphosphate are commonly used peptizers.

The amount of peptizer present will vary with the specific agent, the specific clay, the amount of clay present, and in some cases the other components present.

THE GELS

1. Gels without Peptizer Agent

Hectorite clays and water upon vigorous stirring form an aqueous colloidal solution; if enough clay is present, a gel is formed.

The gel composition may include essences coloring agents, either dissolved or in suspension; or oils such as those used in cosmetics.

The amount of clay used is dependent on the specific clay, the amount of humectant, if any, and the amounts, if any, of other components present in the composition and the gel rigidity desired.

2. Gels from Peptized Solutions

It has been discovered that a thin, water fluid composition consisting essentially of water, hectorite clay, and peptizer is changed to a gel by heating the fluid solution to a gelling temperature. Time is needed for the change to take place and the time is temperature- and peptizer-dependent.

The change to the gel condition takes place even when the fluid solution includes humectant, foaming agents, or other components, or any combination of these. It is to be understood that the presence of other components may cause the composition to lose its thin, watery fluid condition; however, the other components will not cause the fluid solution-other component composition to gel.

The amount of peptizer used will vary with the specific agent, the specific clay and the amount of clay present, and even the other components present as these can effect the gelling capacity of the clay.

CAPSULES AND PARTICLES

The gel composition of this invention includes suspended therein particles and capsules having a size above colloidal dimensions. The particles or capsules may be made in situ by the hereinafter described procedure. In general, particles consist solely of a water insoluble reaction product, whereas capsules include a payload (core) surrounded by a membrane (shell or wall). It must be understood that both payload and membrane (or the particle) must be acceptable for use in cosmetics.

The payload may be any material, liquid, semisolid, or solid, which is useful in the specific gel composition such as essences, colorings, and the like. The payload containing capsules are especially useful when the payload is water insoluble and it is desired that the "carrier", as in a skin cream be an aqueous gel medium. It is evident that capsules are particularly useful when a mixture of materials is desired with the effect being aesthetic and/or practical by avoidance of intermingling.

The particles and capsules are prepared by the reaction of (1) aqueous colloidal solutions of hectorite clay, and (2) certain polar group affording materials.

1. POLAR GROUP AFFORDING ORGANIC MATERIALS

Not every polar group affording organic material is suitable for use. Only those polar group affording organic materials are suitable which react with hectorite clay, in aqueous colloidal solution, to form water insoluble particles. For example, the lower molecular aliphatic alcohols, especially those having high solubility in water, do not react to form water insoluble particles; indeed, these compounds appear to solubilize the clay. It has been observed that cellulose derivatives may or may not react to form water insoluble particles. It is thought that steric hindrance may be the reason for this failure.

It is thought that because the clay in aqueous solution forms a sort of network with reactive sites distributed thereon, the polar group affording polymers, or even macromolecules, may or may not be able to react to form water insoluble particles; reaction seems to be dependent on the spacing of the polymer polar groups, and also on steric hindrance. In some, the polar group spacing is to far out of line with reactive sites of the clay to permit enough reaction to form the water insoluble particles.

The operative polar group affording organic materials cannot be defined merely by naming classes of polar group affording organic materials; each class contains some members that do not react with the aqueous colloidal solution of inorganic silicate.

A simple screening procedure has been devised for determining whether or not a particular polar group affording organic material will react with the aqueous colloidal solution of clay to form water insoluble particles.

One definition is, the polar group affording organic material is characterized by (1) the ability to form water insoluble particles having a size above colloidal dimensions when added to an aqueous colloidal solution of synthetic hectorite clay and tetrasodium pyrophosphate peptizing agent, with commingling, and (2) having been selected from the group consisting of (i) simple organic compounds having at least one polar group and (ii) organic hydrophilic colloids.

Another definition, of equal scope to that above, is in the form of "named classes of compounds". Here, the reactive polar group affording organic compounds are selected from the group consisting of (a) simple organic compounds having at least one polar group, desirably these are further characterized by insubstantial solubility in water at ordinary temperatures; (b) water soluble alkali metal carboxyalkylcellulose and water soluble alkali metal carboxyalkylhydroxyalkylcellulose; (c) water soluble polysaccharides; (d) water soluble proteins; (e) water soluble resins: poly(vinyl alcohol), poly(ethyleneimine), poly(acrylamide), polyvinylpyrrolidone, sulfonated polymers, carboxylic polymers, their esters and alkali metal salts, and maleic copolymer derivatives; and (f) water soluble cellulose ethers.

In general, the preparation of the composition will be carried out at ordinary temperatures of about 15°–43° C. Insubstantial solubility or immiscibility appears to aid in the formation of water insoluble particles when the polar compound is added to the aqueous colloidal solution of clay.

"Water soluble" when used herein as part of the name of a polar group affording organic material is intended to be understood as used in the hydrophilic colloid art, that is, those materials forming colloidal solutions or stable swollen dispersions in water. In the main these materials have solubilities up to about 5 weight percent; some dissolve to a greater extent.

Water soluble polysaccharides are included herein in the understanding of the hydrophilic colloid art. This grouping includes starch and its chemically modified forms, such as, carboxymethylstarch, hydroxyethylstarch, and hydroxypropylstarch; pectin; the plant gums, such as arabic, guar, tragacanth, larch, karaya, and locust bean; the marine polysaccharides, such as, agar, alginate and carrageenan; fully synthetic polysaccharides with properties similar to the natural gums are now available and are included herein.

Water soluble proteins are included herein as understood by the colloid art; gelatin and casein are the best known.

Poly(vinyl alcohol), poly(ethyleneimine), poly(acrylamide), and polyvinylpyrrolidone are well known hydrophilic colloids and are available in many molecular weights.

Carboxylic polymers, their esters and alkali metal salts are available for polyacrylic acid, polymethacrylic acid, polyethacrylic acid, and hydrolysis products of maleic polymers. Alkali metal salts are available as produced from polymers such as poly(acrylamide) and poly(acrylonitrile).

Maleic copolymer derivatives provide water soluble polar polymers such as half-amides and half-esters, available commercially.

Sulfonated polymers are available from the sulfonation of insoluble polymers or from polymerization of monomers having sulfonate groups.

The water soluble alkali metal carboxyalkylcellulose is exemplified by sodium carboxyethylcellulose and sodium carboxymethylcellulose (commonly referred to as CMC). The water soluble alkali metal carboxyalkylhydroxyalkylcellulose is exemplified by sodium carboxymethylhydroxyethylcellulose. Commonly "alkyl" in these cellulosics has 1-3 carbon atoms. (Because of the presence of the carboxy groups, these cellulosics are not considered to be cellulose ethers.)

Water soluble cellulose ethers as used herein are hydrophilic colloids of the type alkylcellulose and hydroxyalkylcellulose and hybrids of these two. Exemplary are methylcellulose, ethylcellulose, methylethylcellulose, hydroxyethylcellulose, ethylhydroxyethylcellulose, and methyhydroxypropylcellulose. Commonly "alkyl" in the cellulose ethers has 1-3 carbon atoms.

Also suitable are the simple organic compounds having at least one polar group, which react with the clay to form water insoluble particles. The simple organic compounds are distinguished from the macromolecules and polymers. Preferred polar groups are hydroxyl and carboxyl. Desirably, the simple organic compounds have insubstantial solubility in water at ordinary temperatures, that is, readily form a separate organic compound phase distinct from the aqueous phase.

However, some compounds having substantial solubility in water may be useful in situations where a nonpolar water immiscible material is to become part of the water soluble particle, that is, a payload containing capsule. The polar compound must be preferentially soluble in the non-polar water immiscible material.

Illustrative groups of simple organic polar compounds are: the aliphatic alcohols, monohydric, dihydric and polyhydric; the lower aliphatic carboxylic acids and the fatty acids. The aliphatic and aromatic amines and amides, and the esters and salts of these compounds.

"Organic hydrophilic colloid" as used herein is intended to mean: any organic compound capable of forming stable suspensions in water of particles having colloidal dimensions — smaller than one micron — or capable of forming colloidal solutions.

2. THE CLAY

The clay for use in making the capsules and the water phase is hectorite, either natural or synthetic. Synthetic hectorite clay is preferred.

3. THE SCREENING PROCEDURE

The screening procedure uses a standard aqueous colloidal clay solution; this clay reacts rapidly at ordinary room temperatures with simple spatula stirring of the 'test' polar group affording organic material. Visual observation of the contents of the transparent bottle in which the procedure is performed is sufficient to show the formation of water insoluble particles of greater than colloidal size.

The standard solution is made up as follows: One part by weight of tetrasodium pyrophosphate peptizer agent is dissolved in (90) parts by weight of water; then (9) parts by weight of Baroid synthetic fluorine (1.8%) hectorite clay (BARSYM LIH-200) are added to the peptized water; the peptized water and the clay are agitated for (8) hours with a Cowles blade at about 1,000 rpm to ensure the formation of a thin, watery fluid aqueous colloidal solution; (40) parts by weight of the aqueous colloidal solution are blended with (60) parts by weight of water to form the standard solution which consists of, in weight percent, water, 96.0; clay, 3.6; and tetrasodium pyrophosphate, 0.4. The standard solution is translucent with a faint bleached-straw color.

The analysis of the standard clay is shown in Table 1, supra. It has: a base exchange capacity (meq/100 g) of 60–70; a color and appearance of a fine, white powder; screen analysis is —200 mesh; the bulk density is 60 lb/cu ft; and the pH of a 15 centipoise solution is 9.5. It has been observed that clay deviating somewhat from the foregoing analysis can be used successfully in the screening procedure.

In the screening procedure, 100 cc of the standard clay solution is placed in a transparent bottle, typically a screw cap bottle of about 300 cc volume. Then about 25 cc of the specific polar material being tested is added to the bottle. If the specific polar material is a liquid, it is added "as is". If it is a solid, it is dissolved in water and 25 cc, sometimes 50 cc as a check, is added to the bottle. Usually the commingling imparted by the pouring of the test material into the bottle is enough to produce water insoluble particles — if the test material is reactive. Otherwise a mild shaking of the contents is sufficient. In most cases direct visual observation sees the water insoluble particles, very small particles can be detected by viewing the wetted interior surface of the bottle by transmitted light. This indirect viewing overcomes the obstruction of a colored aqueous solution, or confirms the absence of particles.

ILLUSTRATION I. PARTICLES

Hydroxyethylcellulose (Cellosize QP4400, trademark of Union Carbide Corporation) was dissolved in water to give a two (2) weight percent solution; this solution was a transparent, water-white liquid. Fifty (50) cc of the 2% solution was poured in 100 cc of the standard clay solution and gently stirred with a spatula. Immediately the visual appearance of the contents changed to a turbid gray slurry. After turning the bottle sideways, gray strands were observed on the wetted interior surface. These strands were a graytan color, 2–3 mm wide and 6–15 mm long. The water insoluble strand drifted in the continuous aqueous phase and settled very slowly. During shelf over some time, there was no detectable merging (coalescence) of the strands; they retained their discrete nature.

Having discussed the broad aspects of the present invention, reference is had to the following Example of the preparation of the composition of the present invention. In the Example, certain ingredients are shown by trademark, the composition of these ingredients being as follows:

| | |
|---|---|
| Cellosize WP-4400-L | hydroxyethyl cellulose |
| Rheo-Vis | A hectorite clay |
| LS-207 | |
| Methyl paraben | a mixture of parabens |
| Span 65 | sorbitan tristearate |
| Myrj 52 | polyoxyethylene stearate |
| Giv-Tan F | 2-ethoxyethyl-p-methoxycinnamate |
| Wickenol 155 | (octyl palmitate) 2-ethylhexyl palmitate) |
| Escalol 507 | 2-ethylhexyl-p-dimethylaminobenzoate |
| Marcol 70 | white mineral oil |
| Glyco-Lipo Proteinic Complex | a hydrolyzed animal fatty-protein complex |

EXAMPLE 1

The encapsulated sunscreen agent, Phase C, contains the following ingredients in percent by weight:

| | |
|---|---|
| Phase 1 | |
| Cellosize WP-4400-L | 0.10 – 3.00 |
| Propylene glycol | 1.00 – 20.00 |
| Deionized water | qs. 100 |
| Phase 2 | |
| Rheo-Vis 43-A (Clay) | 0.10 – 10.00 |
| Sodium acid pyrophosphate (food grade) | 0.05 – 2.00 |
| Deionized water | 22.5 |
| Phase 3 | |
| Iron oxide pigment | 0.50 – 15.00 |
| LS-207-B | 0.30 |
| Methyl paraben | 0.10 |
| Giv-Tan F | 0.25 – 5.00 |

Make Phase 1 by charging the propylene glycol to a suitable stainless steel vessel equipped with a variable speed Lightnin' Mixer. With the mixing running at high speed, disperse the Cellosize very well until uniform. Add the water.

Make Phase 2 by adding water to a separate container equipped with a variable speed Lightnin' Mixer. With the mixer running at fairly high speed, add sodium acid pyrophosphate and disperse well.

Add the ingredients of Phase 3 to Phase 1 and stir until uniform. Then add Phase 2 to Phase 1 and stir until uniform. Pass the mixture through a colloid mill until smooth.

It should be noted that the proportions given include ranges of ingredients which are operable. It is preferred that the Rheo-Vis clay be present in an amount of 2.25 percent and the sodium acid pyrophosphate be present in an amount of 0.25 percent.

EXAMPLE 2

A normal protection suntan cream includes the following ingredients in percent by weight:

| Phase A | |
|---|---|
| Glyceryl monostearate | 0.50 – 5.00 |
| Cetyl alcohol | 0.50 – 5.00 |
| Span 65 | 0.10 – 3.00 |
| Myrj 52 | 0.10 – 2.50 |
| Wickenol 155 | 2.00 – 25.00 |
| Isostearic acid | 0.50 – 5.00 |
| Giv-Tan F | 0.10 – 5.00 |
| Escalol 507 | 0.10 – 5.00 |
| Marcol 70 | 1.00 – 25.00 |
| Phase B | |
| Rheo-Vis 43-A | 0.10 – 7.50 |
| Sodium acid pyrophosphate | 0.10 – 7.50 |
| Propylene Glycol | 1.00 – 15.00 |
| LS-207/B | 0.30 |
| Methyl paraben | 0.10 |
| Triethanolamine | 0.25 – 2.50 |
| Glyco-Lipo Protein Complex | 0.10 |
| Deionized water | qs. 100 |
| Phase C | |
| Encapsulated sunscreen agent (from Example 1) | 0.05 – 2.00 |
| Perfume 573-Bis | 0.20 |

Phase B is first made in a suitable vessel equipped with a mixer such as a Silverson Mixer and counter-rotating stirrers. The Silverson Mixer is started, and the sodium acid pyrophosphate is added and dispersed well. The clay is sprinkled in and stirred well until completely hydrated. In a separate stainless steel vessel, the propylene glycol is charged, and the LS-207/B and methyl paraben are dissolved therein. The propylene glycol is added to the hydrated clay mixture. The triethanol amine and protein complex are then added.

In a separate stainless steel steam-jacketed kettle, all the ingredients of Phase A are added. Both Phases A and B are heated to 75° C. The Silverson Mixer is kept going in Phase B while the heating is conducted.

When both Phases A and B are at 75° C., Phase A is strained through silk into Phase B while stirring with the Silverson Mixer. Stirring is continued for 10 minutes, and the mixture is allowed to cool for 15 minutes. The Silverson mixture is removed and replaced with a variable-speed Lightnin' Mixer. With the Lightnin' Mixer going at a moderately fast speed, but without aerating, Phase C is added, and stirring is continued until the particles break up to the desired size. Stirring is continued until the mixture is cooled to about 30° C.

If the above procedure that is, adding Phase C with the Lightnin' Mixer operating, does not result in small enough particles of encapsulated active ingredient, a second method may be used. In this method, a small portion of the emulsion of Phases A and B can be withdrawn into a small vessel and Phase C incorporated therein and dispersed with a Lightnin' Mixer until the desired particle size is reached. The contents of this vessel can then be incorporated into the emulsion and dispersed merely with counter-rotating stirrers.

EXAMPLE 3

A preferred composition for a normal protection suntan cream is as follows, in percent by weight:

| Phase A | |
|---|---|
| Glyceryl monostearate | 2.5 |
| Cetyl alcohol | 2.0 |
| Span 65 | 0.5 |
| Myrj 52 | 0.25 |
| Wickenol 155 | 8.0 |
| Isostearic acid | 2.0 |
| Giv-Tan F | 0.75 |
| Escalol 507 | 0.75 |
| Marcol 70 | 4.0 |
| Phase B | |
| Rheo-Vis 43-A | 2.25 |
| Sodium acid pyrophosphate | 0.25 |
| Propylene Glycol | 5 |
| LS-707/B | 0.3 |
| Methyl paraben | 0.1 |
| Triethanolamine | 1.0 |
| Glyco-Lipo Protein Complex | 0.1 |
| Deionized water | qs. 100 |
| Phase C | |
| Encapsulated sunscreen agent (from Example 1) | 0.12 |
| Perfume 573-Bis | 0.2 |

The procedure for making the composition was the same as in Example 2.

EXAMPLE 4

A sunscreen composition for use by people with fair or sun-sensitive skin is made as in Example 2, with the proportion of Giv Tan F being from 0.25 to 5.0 percent and Escalol 507 being from 0.25 to 5.0 percent.

EXAMPLE 5

A preferred composition of a maximum protection sunscreen composition for people with sensitive skin is made as in Example 3, with the proportion of certain ingredients being changed. Except where noted below, all the other ingredients are the same as in Example 3, and the procedure for making the composition is the same. The ingredients listed below with proportions in percent by weight are the only deviation from the proportions shown in Example 3:

| Glyceryl monostearate | 2.25 |
|---|---|
| Cetyl alcohol | 1.5 |
| Giv-Tan F | 1.25 |
| Escalol 507 | 1.75 |

EXAMPLE 6

Another embodiment of the invention is a sunscreen composition as already described with, in addition, titanium dioxide and iron oxide pigments to add a bronze coloration to the cream base. This composition includes the following ingredients, in percent by weight:

| Phase A | |
|---|---|
| Glyceryl monostearate | 0.25 – 5.00 |
| Cetyl alcohol | 0.50 – 5.00 |
| Span 65 | 0.10 – 3.00 |
| Myrj 52 | 0.10 – 2.50 |
| Wickenol 155 | 2.00 – 35.00 |
| Isostearic acid | 0.50 – 5.00 |
| Giv-Tan F | 0.10 – 5.00 |
| Escalol 507 | 0.10 – 5.00 |
| Phase B | |
| Rheo-Vis 43-A | 2.25 |
| Sodium acid pyrophosphate | 0.10 – 7.50 |
| Propylene Glycol | 1.00 – 15.00 |
| LS-207/B | 0.30 |
| Methyl paraben | 0.10 |
| Triethanolamine | 0.25 – 2.50 |
| Glyco-Lipo Protein Complex | 0.10 |
| Deionized water | qs. 100 |
| TiO$_2$ and FeO Pigments | 0.25 – 7.50 |
| Phase C | |
| Encapsulated sunscreen agent (from Example 1) | 0.05 – 2.00 |

-continued

| | |
|---|---|
| Perfume 573-Bis | 0.20 |
| Titanium dioxide and iron oxide pigments | 0.25 – 7.50 |

The bronzing sunscreen composition is made in a manner similar to the composition of Example 2. Phase B is first made by charging the water to a suitable vessel equipped with a Silverson stirrer and counter-rotating mixers. The stirrer is started and the sodium acid pyrophosphate is added and dispersed well. The clay is sprinkled in and stirred well until completely hydrated. In a separate stainless steel vessel, the LS-207/B and methyl paraben are dissolved in the propylene glycol. This mixture is then added to the hydrated clay. The triethanolamine and protein complex are added with stirring. The titanium dioxide and iron oxide pigments are then added and stirred until uniform. A colloid mill is set at 0.004 and the mixture of Phase B is recirculated through the mill and back into the kettle. It is then slowly heated to 75° C.

In another stainless steel steam-jacketed kettle, all the ingredients of Phase A are charged, mixed, and heated to 75° C. When both phases are at 75° C., Phase A is strained through silk into Phase B, with the mixer going. Stirring is continued for 10 minutes, and the mixture is allowed to cool to 55° C. The perfume is added and dispersed well. The mixture is cooled to 50° C., and the Silverson stirrer is replaced with a variable-speed Lightnin' Mixer. With the Lightnin' Mixer turned on, Phase C is added. Stirring is continued until the particles are the desired size.

EXAMPLE 7

A preferred bronzing sunscreen composition contains the following ingredients, in percent by weight:

| | |
|---|---|
| Phase A | |
| Glyceryl monostearate | 1.75 |
| Cetyl alcohol | 1.0 |
| Span 65 | 2.5 |
| Myrj 52 | 0.25 |
| Wickenol 155 | 17.0 |
| Isostearic acid | 2.0 |
| Giv-Tan F | 0.75 |
| Escalol 507 | 0.75 |
| Phase B | |
| Rheo-Vis 43-A | 2.25 |
| Sodium acid pyrophosphate | 0.25 |
| Propylene Glycol | 5.0 |
| LS-207/B | 0.30 |
| Methyl paraben | 0.10 |
| Triethanolamine | 1.0 |
| Glyco-Lipo Protein Complex | 2.0 |
| Deionized water | qs. 100 |
| Phase C | |
| Encapsulated sunscreen agent (from Example 1) | 0.05 |
| Perfume 573-Bis | 0.20 |
| Titanium dioxide and iron oxide pigments | 2.0 |

The mixing procedure is the same as in Example 6.

It should be apparent from the foregoing detailed description that the objects set forth above have been successfully achieved. Moreover, while there is shown and described a present preferred embodiment of the invention, it is to be distinctly understood that the invention is not limited thereto but may be otherwise variously embodied in practice within the scope of the following claims.

What is claimed is:

1. An ultraviolet sunscreening composition for protection against the harmful rays of the sun comprising an oil phase, a water phase, and an encapsulated active base:
   (A) said oil phase comprising an effective amount of an emulsifier, an effective amount of an emollient, and an effective amount of a non-ionic surfactant;
   (B) said water phase comprising, in parts by weight, 0.10–7.50 parts of hectorite clay, 0.10–7.50 parts of a peptizer for said hectorite clay, 1.00–15.00 parts of a humectant, 0.10 parts of a hydrolyzed animal fatty protein complex, and water; and
   (c) said encapsulated active base comprising, in parts by weight, 0.10–10.00 parts of hectorite clay; 0.10–3.0 parts of a polar group affording organic compound (1) characterized as being reactable with said hectorite clay to form water-insoluble particles having a size above colloidal dimensions when added to an aqueous colloidal solution of synthetic hectorite clay and tetrasodium pyrophosphate and (2) selected from the group consisting of a simple organic compound having at least one polar group characterized by insubstantial solubility in water at ordinary temperatures and (3) organic hydrophilic colloid; 0.05–2.00 parts of a peptizer for said clay; an effective amount of a sunscreen agent; and water.

2. A composition as claimed in claim 1, wherein:
   (A) said oil phase comprises glyceryl monostearate, cetyl alcohol, 2-ethylhexyl palmitate, isostearic acid, polyoxyethylene stearate, and sorbitan stearate;
   (B) said water phase comprises said hectorite clay, said peptizer, propylene glycol as said humectant, triethanolamine, said protein, and said water; and
   (C) said encapsulated active base comprises said hectorite clay, hydroxyethyl cellulose as said polar group affording compound, said peptizer, and said water.

3. A composition as claimed in claim 2, wherein said hectorite clay is synthetic hectorite clay, said synthetic hectorite clay is present in said water phase in a gel-forming amount of about 0.10 to about 7.50 percent by weight, said peptizer is sodium acid pyrophosphate and said sodium acid pyrophosphate is present in said water phase in an amount of about 0.10–7.50 percent by weight.

4. A composition as claimed in claim 2, wherein said oil phase further comprises a sunscreen agent and mineral oil.

5. A composition as claimed in claim 2, wherein said encapsulated active base further includes iron oxide pigment.

6. A composition as claimed in claim 2, comprising:
   (A) an oil phase comprising, in parts by weight:

| | |
|---|---|
| glyceryl monostearate | 0.25 – 5.00 |
| cetyl alcohol | 0.50 – 5.00 |
| 2-ethylhexyl palmitate | 2.00 – 35.00 |
| isostearic acid | 0.50 – 5.00 |
| polyoxyethylene stearate | 0.10 – 2.50 |
| sorbitan tristearate | 0.10 – 3.00 |
| sunscreen agent | effective amount |

(B) a water phase comprising, in parts by weight:

| | |
|---|---|
| synthetic hectorite clay | 0.10 – 7.50 |
| sodium acid pyrophosphate | 0.10 – 7.50 |
| propylene glycol | 1.00 – 15.00 |
| a preservative | effective amount |
| triethanolamine | 0.25 – 2.50 |

-continued

| | |
|---|---|
| a hydrolyzed animal fatty protein complex | 0.10 |
| water | balance to make 100; and |

(C) about 0.1 part of an encapsulated active base which consists essentially of, in percent by weight:

| | |
|---|---|
| hydroxyethyl cellulose | 0.10 – 3.00 |

-continued

| | |
|---|---|
| synthetic hectorite clay | 0.10 – 10.00 |
| sodium acid pyrophosphate | 0.05 – 2.00 |
| propylene glycol | 1.00 – 20.00 |
| iron oxide pigment | 0.50 – 15.00 |
| sunscreen agent | effective amount |
| a preservative | effective amount |
| water | balance. |

7. A composition as claimed in claim 6, wherein said sunscreen agent is at least one member selected from the group consisting of 2-ethoxyethyl p-methoxycinnamate and amyl p-dimethylaminobenzoate.

* * * * *

UNITED STATES PATENT OFFICE
CERTIFICATE OF CORRECTION

Patent No. 4,129,645            Dated December 12, 1978

Inventor(s) Gabriel Barnett, et al

It is certified that error appears in the above-identified patent and that said Letters Patent are hereby corrected as shown below:

Column 2, line 6: "amyl" should be --2-ethylhexyl--.

line 54: After "oxygen" insert --(O)--.

Column 3, line 4: After "mineral" insert a period.

line 59: After "hydroxide" insert a comma.

Column 4, line 24: After "essences" insert a comma.

line 33: Change "disclovered" to --discovered--.

Column 9, line 23: "0.10" is under the wrong column.

lines 36-37: "triethanol amine" should be --triethanolamine--.

Column 10, line 12: "LS-707/B" should be --LS-207/B--.

line 25: "Giv Tan" should be --Giv-Tan--.

UNITED STATES PATENT OFFICE
CERTIFICATE OF CORRECTION

Patent No. 4,129,645  Dated December 12, 1978

Inventor(s) Gabriel Barnett, et al

It is certified that error appears in the above-identified patent and that said Letters Patent are hereby corrected as shown below:

Column 12, line 11: "(c)" should be --(C)--.

Column 14, line 12: "amyl" should be --2-ethylhexyl--.

Signed and Sealed this

Twenty-second Day of May 1979

[SEAL]

Attest:

RUTH C. MASON
Attesting Officer

DONALD W. BANNER
Commissioner of Patents and Trademarks